(12) United States Patent
Mighell et al.

(10) Patent No.: US 9,855,083 B2
(45) Date of Patent: Jan. 2, 2018

(54) BONE PLATE WITH ELEVATED SUTURE HOLE STRUCTURES

(71) Applicant: Extremity Designs, LLC, Tampa, FL (US)

(72) Inventors: Mark Alan Mighell, Tampa, FL (US); Sergio Gutierrez, Tampa, FL (US)

(73) Assignee: EXTREMITY DESIGNS, LLC, Tampa, FL (US)

( * ) Notice: Subject to any disclaimer, the term of this patent is extended or adjusted under 35 U.S.C. 154(b) by 440 days.

(21) Appl. No.: 14/569,401

(22) Filed: Dec. 12, 2014

(65) Prior Publication Data

US 2016/0166298 A1   Jun. 16, 2016
US 2017/0042596 A9   Feb. 16, 2017

Related U.S. Application Data

(60) Provisional application No. 61/915,119, filed on Dec. 12, 2013.

(51) Int. Cl.
   *A61B 17/80*   (2006.01)
   *A61B 17/04*   (2006.01)

(52) U.S. Cl.
   CPC ...... *A61B 17/8061* (2013.01); *A61B 17/0401* (2013.01); *A61B 17/80* (2013.01); *A61B 17/8057* (2013.01)

(58) Field of Classification Search
   CPC .......................... A61B 17/0401; A61B 17/80
   See application file for complete search history.

(56) References Cited

U.S. PATENT DOCUMENTS

2006/0264946 A1*  11/2006  Young .............. A61B 17/1728
                                                   606/915
2009/0264936 A1*  10/2009  Gonzalez-Hernandez ..............
                                            A61B 17/0401
                                                   606/286
2011/0224736 A1*   9/2011  Humphrey ......... A61B 17/1728
                                                   606/289

* cited by examiner

Primary Examiner — Samuel Hanna
(74) Attorney, Agent, or Firm — Shabbi S. Khan; Foley & Lardner LLP

(57) ABSTRACT

The disclosure relates to a bone plate for repairing bone fractures. The bone plate has a first upper surface and a first opposed bone-facing surface. The first bone facing surface is shaped to generally conform to a plate-facing surface of the bone, a bone plate thickness, at least one fastener hole extending between the first upper surface and the first bone facing surface, and a suture hole structure extending from a portion of a boundary or boundary edge of the bone plate and has a second upper surface and a second opposed bone facing surface, a suture hole structure thickness, at least one suture hole extending between the second upper surface and the second bone-facing surface. The suture hole structure thickness is less than the bone plate thickness, and the second bone-facing surface of the suture hole structure is elevated above the first bone-facing surface of the bone plate.

12 Claims, 14 Drawing Sheets

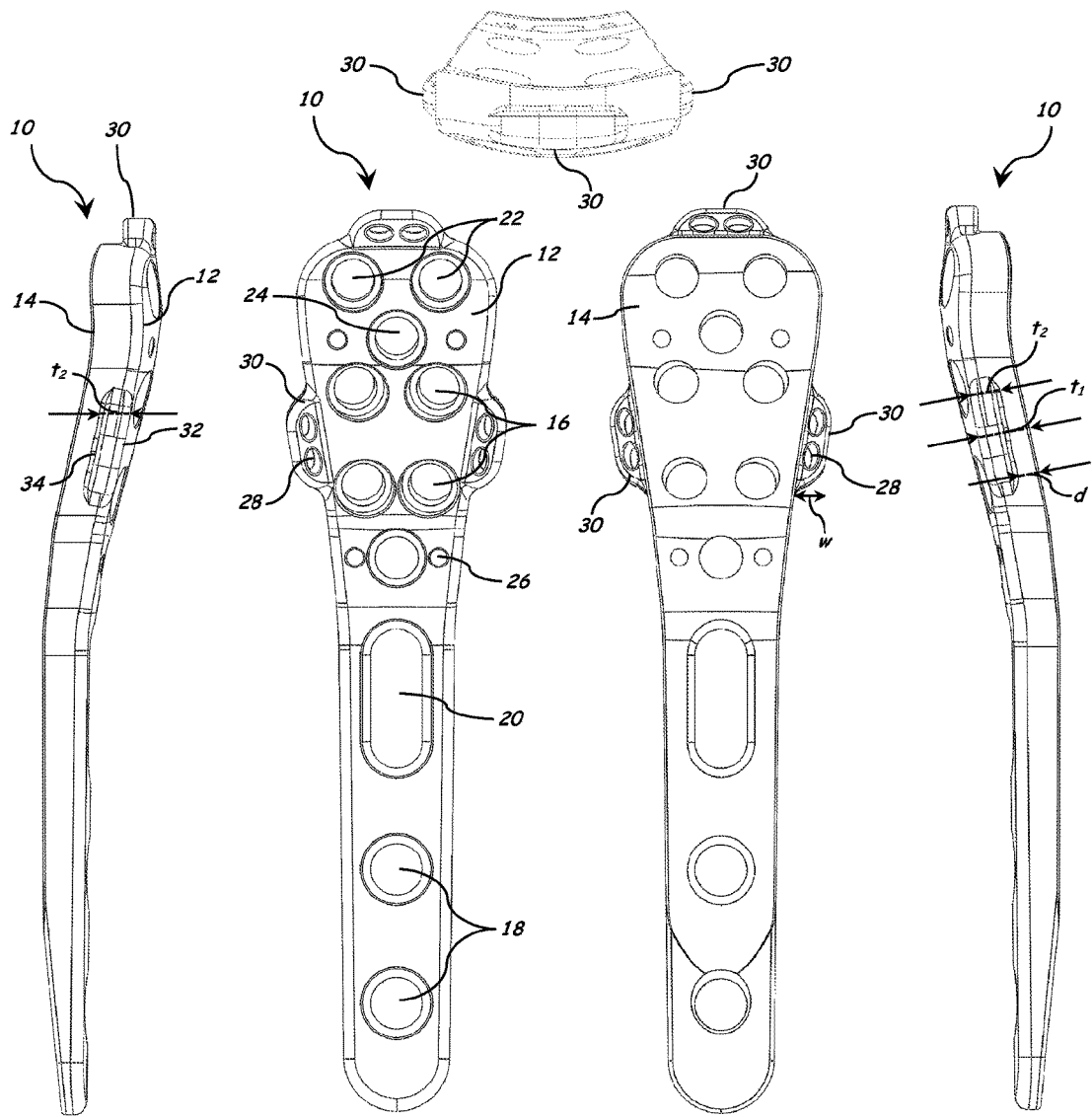
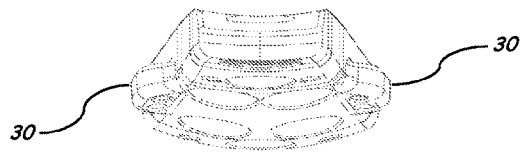
Figure 1C  Figure 1A  Figure 1B  Figure 1D

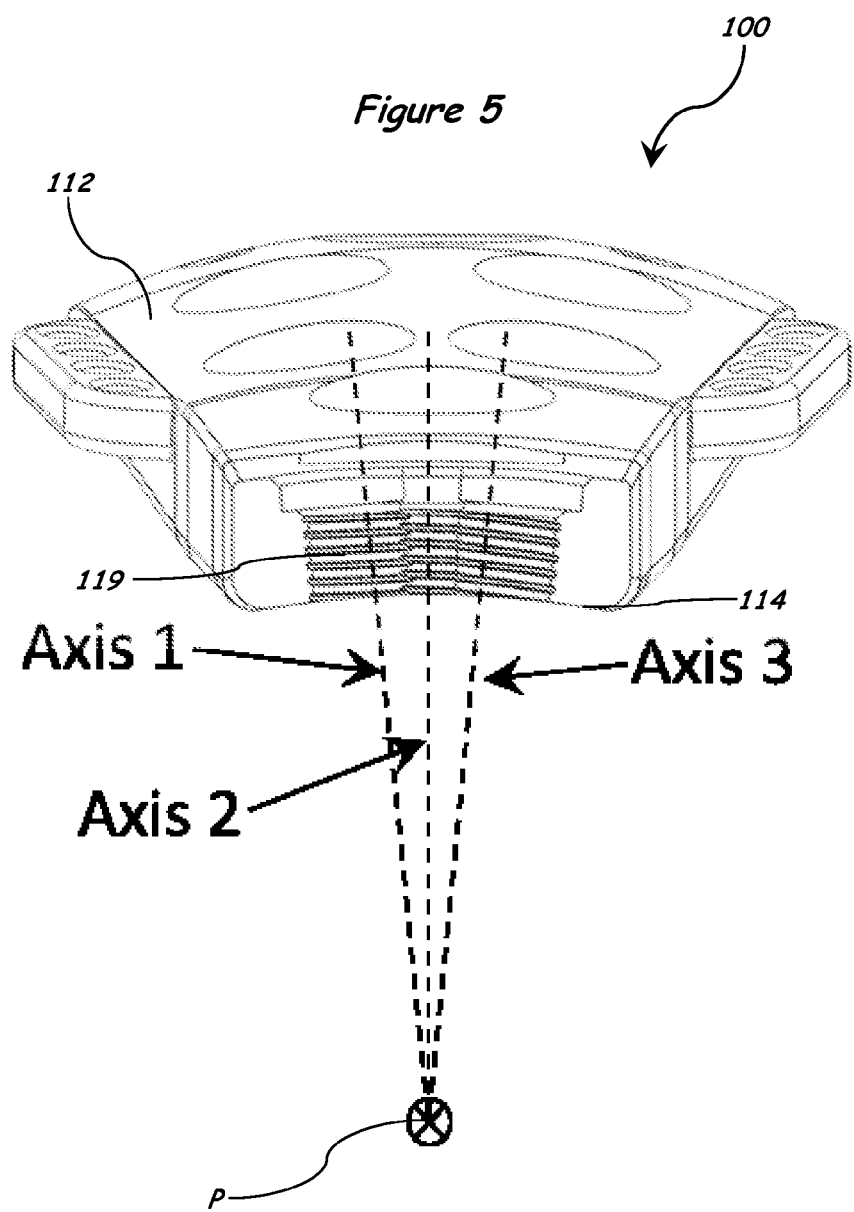

BONE PLATE WITH ELEVATED SUTURE HOLE STRUCTURES

CROSS-REFERENCE TO RELATED APPLICATIONS

The present application claims priority to U.S. provisional patent application Ser. No. 61/915,119, filed Dec. 12, 2013, entitled "Humeral Fracture Plate with Suture Hole Projections", the contents of which are hereby incorporated by reference in their entirety.

FIELD OF INVENTION

This invention relates to a bone plate for use in repairing bone fractures.

BACKGROUND OF THE INVENTION

Proximal humerus fractures are most commonly repaired with open reduction and internal fixation using plates and screws attached via bi-cortical or uni-cortical fixation. The preferred method to gain access to the fracture site is by making a large incision through the skin and muscles. Once the fracture has been exposed, the fragments of bone are approximated to the plate, including fragments that are attached to muscles via tendons. These muscles (e.g., rotator cuff) are attached to the plate via suture holes designed into it. Problems arise when the plate is first attached to the bone since it is difficult to pass the sutures between the plate and the bone. Thus, manufactures have provided bone plates with suture holes including undulations or suture-clearance recesses or lateral channels formed into the bottom surface and the edge of the plate and placed in relative proximity with corresponding suture holes such that a straight or curved suture needle and attached suture material may be passed through the hole even when the plate is fixed to the bone. This solution still presents challenges during surgery as there is insufficient space or clearance between the bone plate and the bone. Additionally, the superior screws often have the problem of exiting the humeral head superiorly, thus these screws must be able to be adjusted inferiorly to be directed completely into the humeral head.

The present invention seeks to remedy these problems. The object of the invention is to provide an internal fixation system with a plate which provides the surgeon with flexibility, ease of use, and operational efficiency such that a suture can be easily and quickly passed through a suture hole.

Another object of the invention is to provide a bone plate that supports both unidirectional and surgeon-directed or omnidirectional fixation of the screws relative to the plate.

SUMMARY OF INVENTION

This invention achieves the objective with a bone plate having a first upper surface and a first opposed bone-facing surface, the first bone-facing surface shaped to generally conform to a plate-facing surface of the bone, a bone plate thickness, at least one fastener hole extending between the first upper surface and the first bone-facing surface, and a suture hole structure extending from at least a portion of a boundary or boundary edge of the bone plate and having a second upper surface and a second opposed bone-facing surface, a suture hole structure thickness, at least one suture hole extending between the second upper surface and the second bone-facing surface, wherein the suture hole structure thickness is less than the bone plate thickness, and the second bone-facing surface of the suture hole structure is elevated above the first bone-facing surface of the bone plate by a distance greater than 0 mm.

In another embodiment of the invention, the second upper surface of the suture hole structure is flush with and, optionally, has a substantially similar contour as the contour of that portion of the first upper surface of the bone plate where the suture hole structure extends from.

In accord with another embodiment, the fastener hole of the bone plate comprises two or more sets of threads with intersecting axes, wherein the angle of each axis is predetermined during manufacturing.

In a further development of the invention, the intersecting axes of sets of threads of the fastener hole lie in a plane substantially parallel to at least one of a longitudinal plane which divides the plate into left and right portions and a transverse plane which divides the bone plate into proximal and distal portions.

Various bone fasteners, such as screws and pegs, can be used with the current invention, for example, those with partially spherical or conical heads with or without external threads engageable with the threads on the inner wall surface of the fastener hole.

These and other features of various embodiments can be understood from a review of the following detailed description in conjunction with the accompanying drawings.

It is to be understood that both the foregoing general description and the following detailed description and accompanying drawings are exemplary and explanatory and are not restrictive of the present invention, as claimed.

BRIEF DESCRIPTION OF THE DRAWINGS

The present invention and its developments will become more fully understood from, but not limited by, the detailed description and the accompanying drawings, wherein:

FIG. 1A shows a top view of a bone plate with elevated suture hole structures;

FIG. 1B shows a bottom view of the bone plate according to FIG.1A;

FIG. 1C shows a side view of the bone plate according to FIG.1A;

FIG. 1D shows another side view of the bone plate according to FIG.1A;

FIG. 1E shows an end view of the bone plate according to FIG.1A;

FIG. 1F shows another end view of the bone plate according to FIG.1A;

FIG. 5 shows a cross sectional view of the bone plate shown in FIG. 3A taken along sectional line 5-5 of FIG. 3A.

DETAILED DESCRIPTION OF THE PREFERRED EMBODIMENT

Figure 2A:
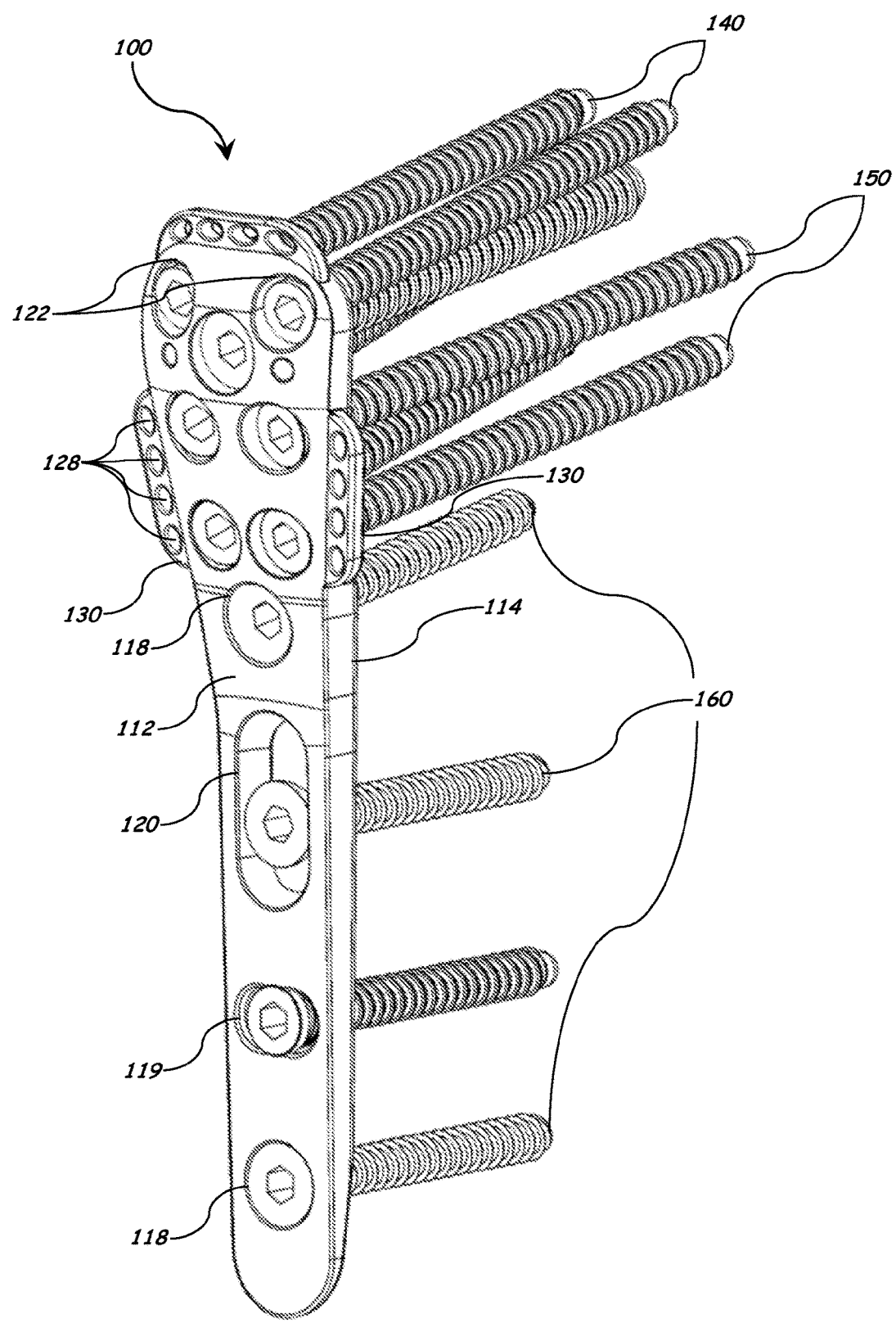
FIG. 2A shows a top perspective view of a bone plate with the bone screws inserted and the top two screws angled superiorly.
Figure 2B:
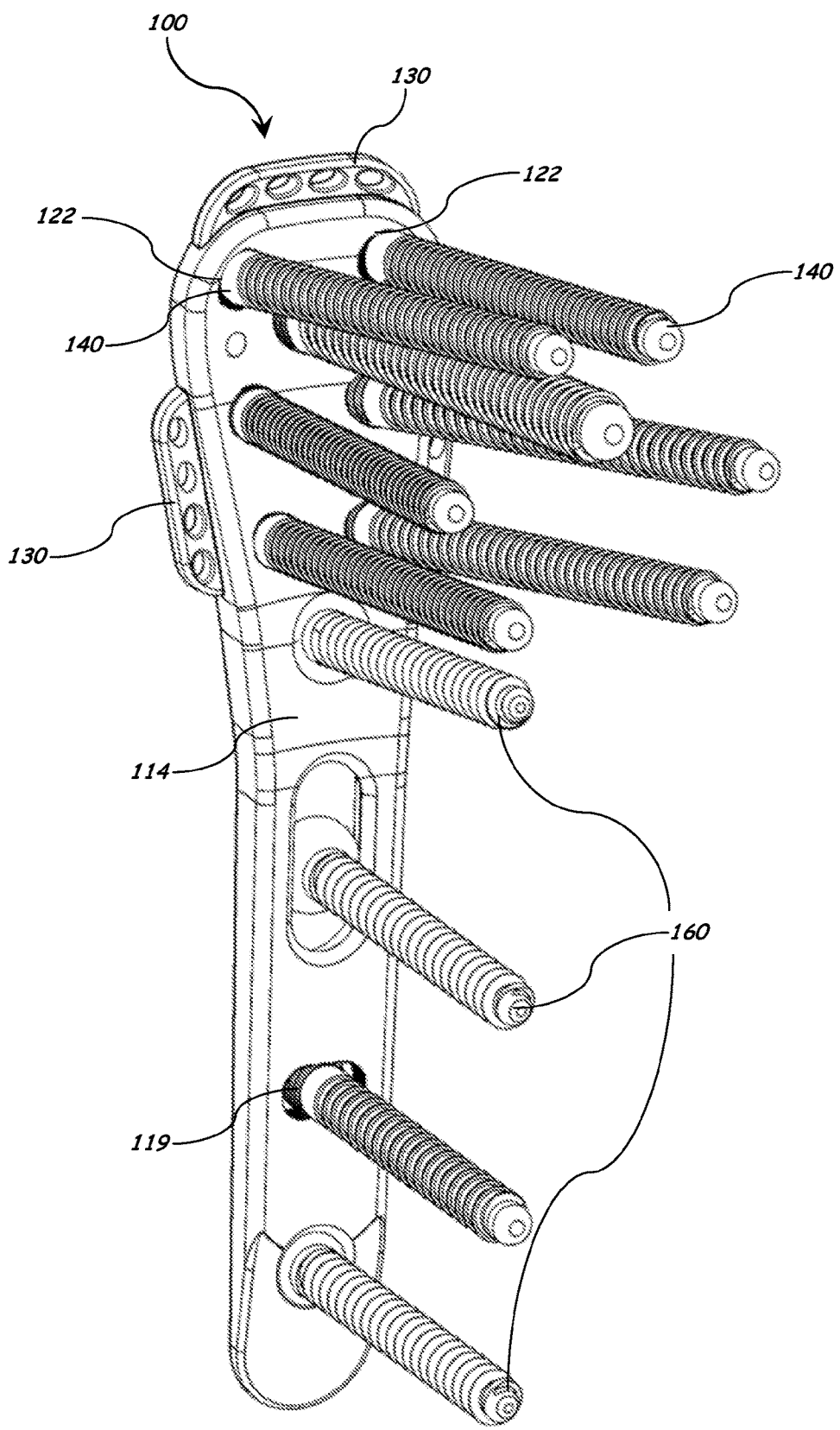
FIG. 2B shows a bottom perspective view of the bone plate according to FIG. 2A.
Figure 2C:
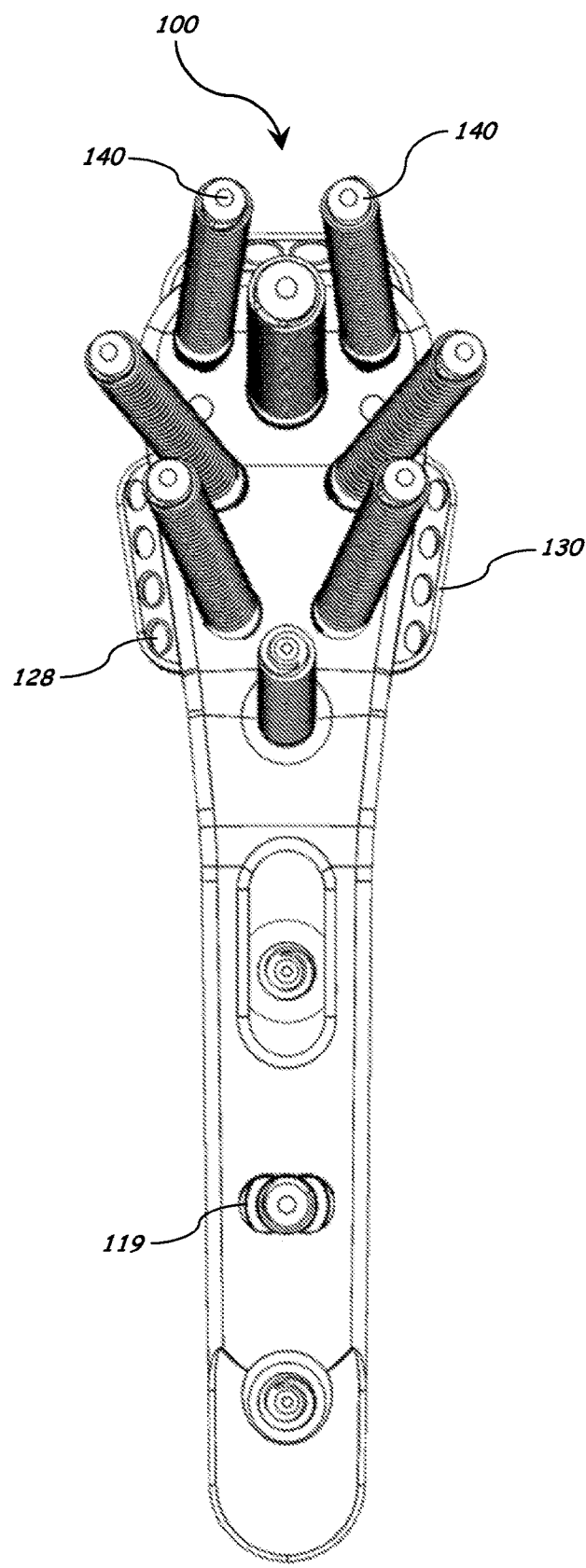
FIG. 2C shows another bottom perspective view of the bone plate according to FIG. 2A.
Figure 2D:
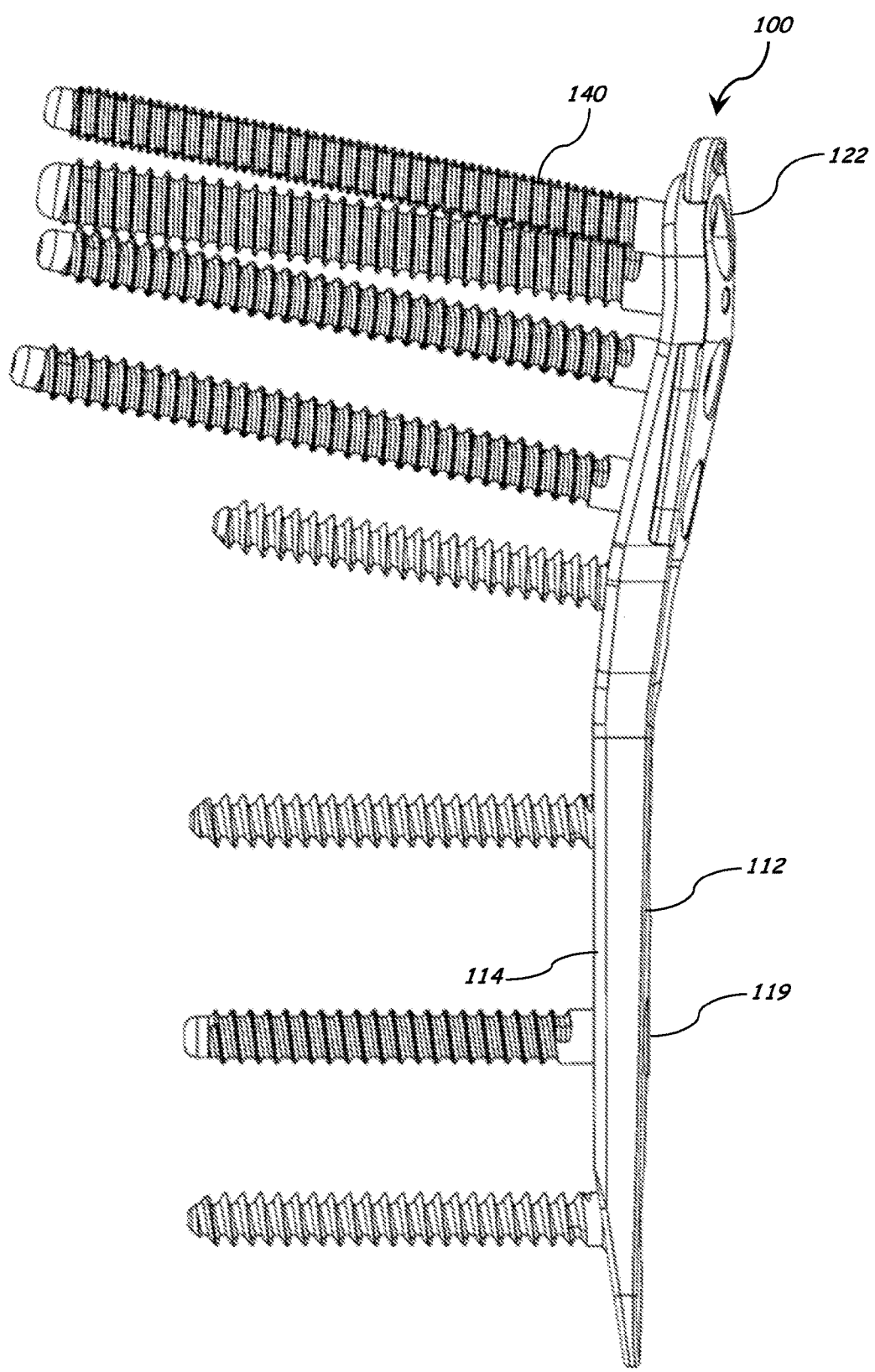
FIG. 2D shows a side perspective view of the bone plate according to FIG. 2A.
Figure 2E:
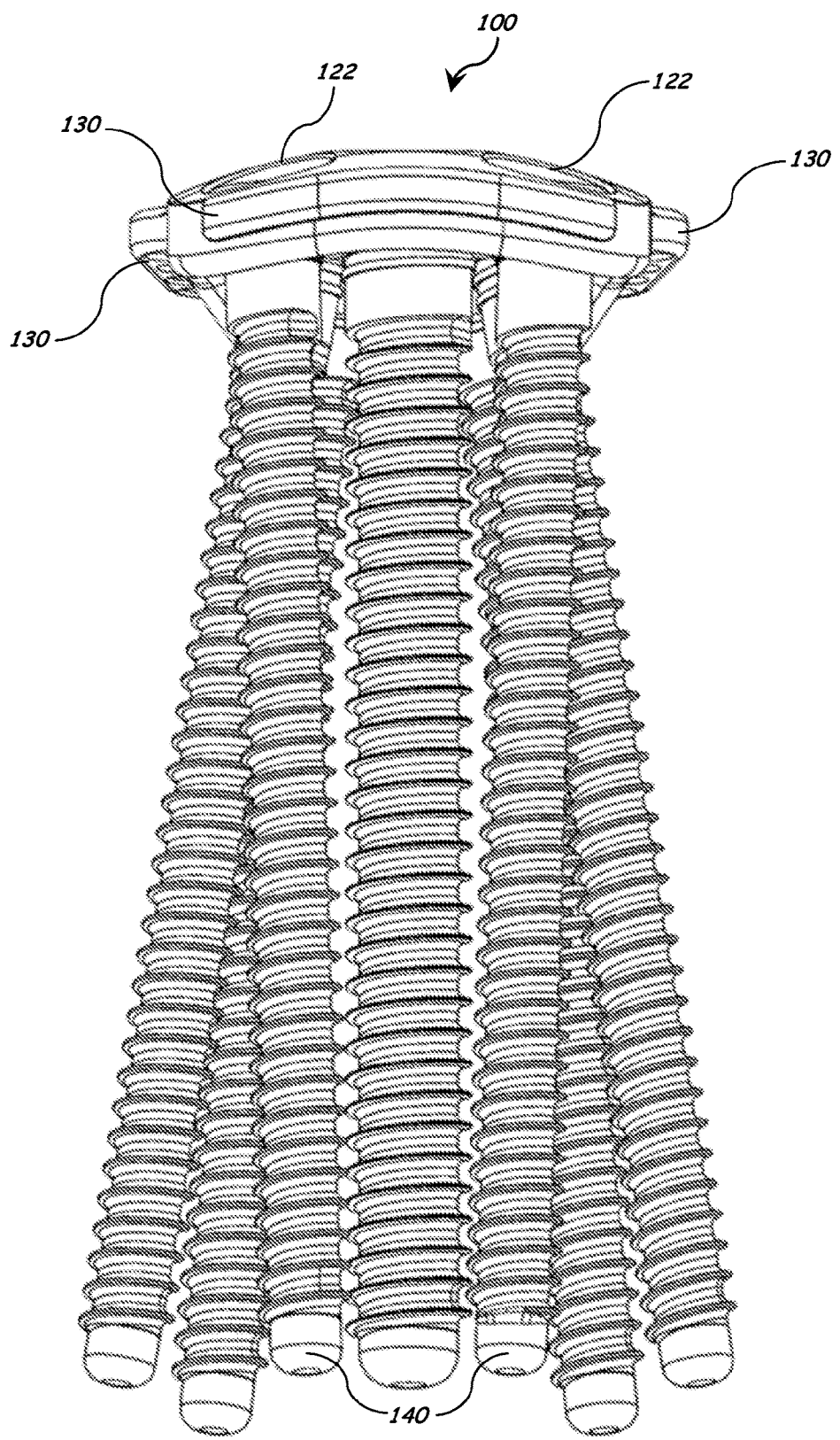
FIG. 2E shows an end perspective view of the bone plate according to FIG. 2A.
Figure 3A:
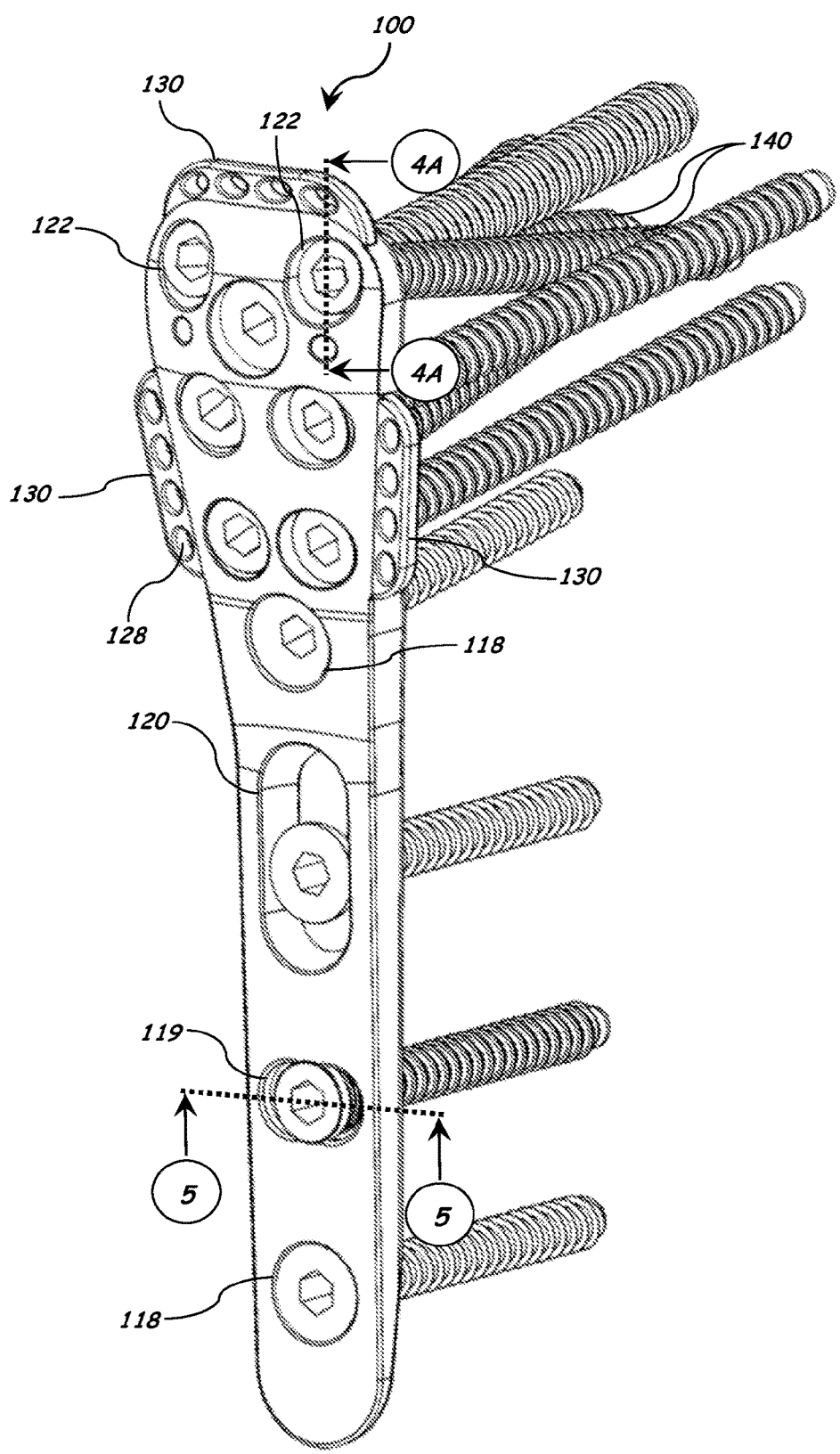
FIG. 3A shows a top perspective view of the bone plate according to FIG. 2A with the top two screws angled inferiorly.
Figure 3B:
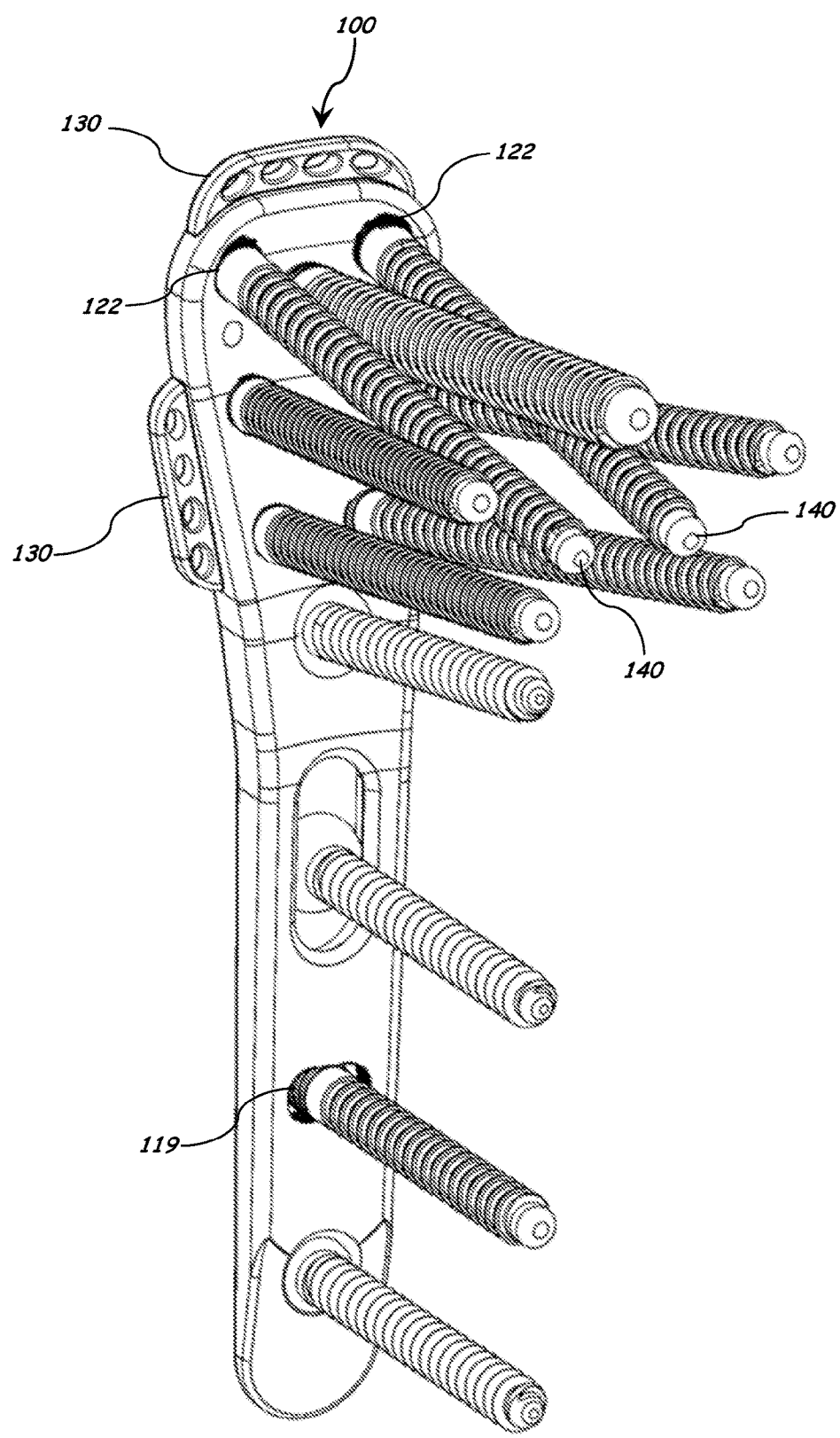
FIG. 3B shows a bottom perspective view of the bone plate according to FIG. 3A.
Figure 3C:
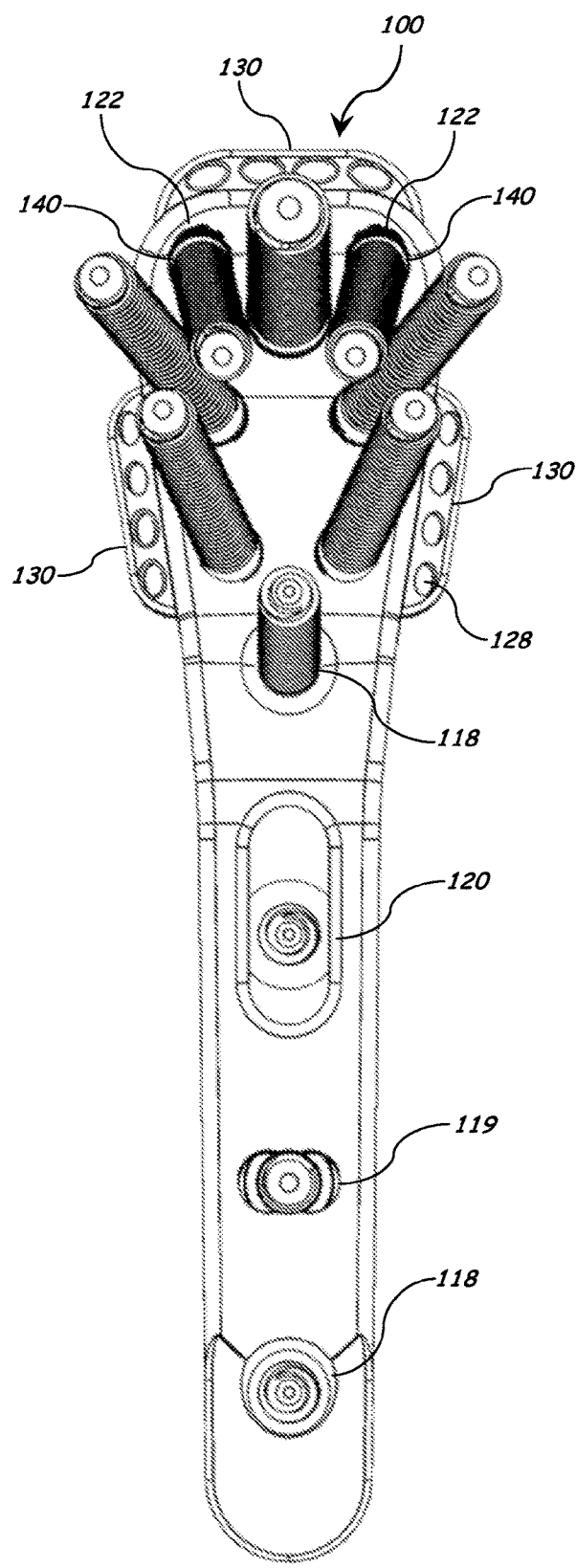
FIG. 3C shows another bottom perspective view of the bone plate according to FIG. 3A.
Figure 3D:
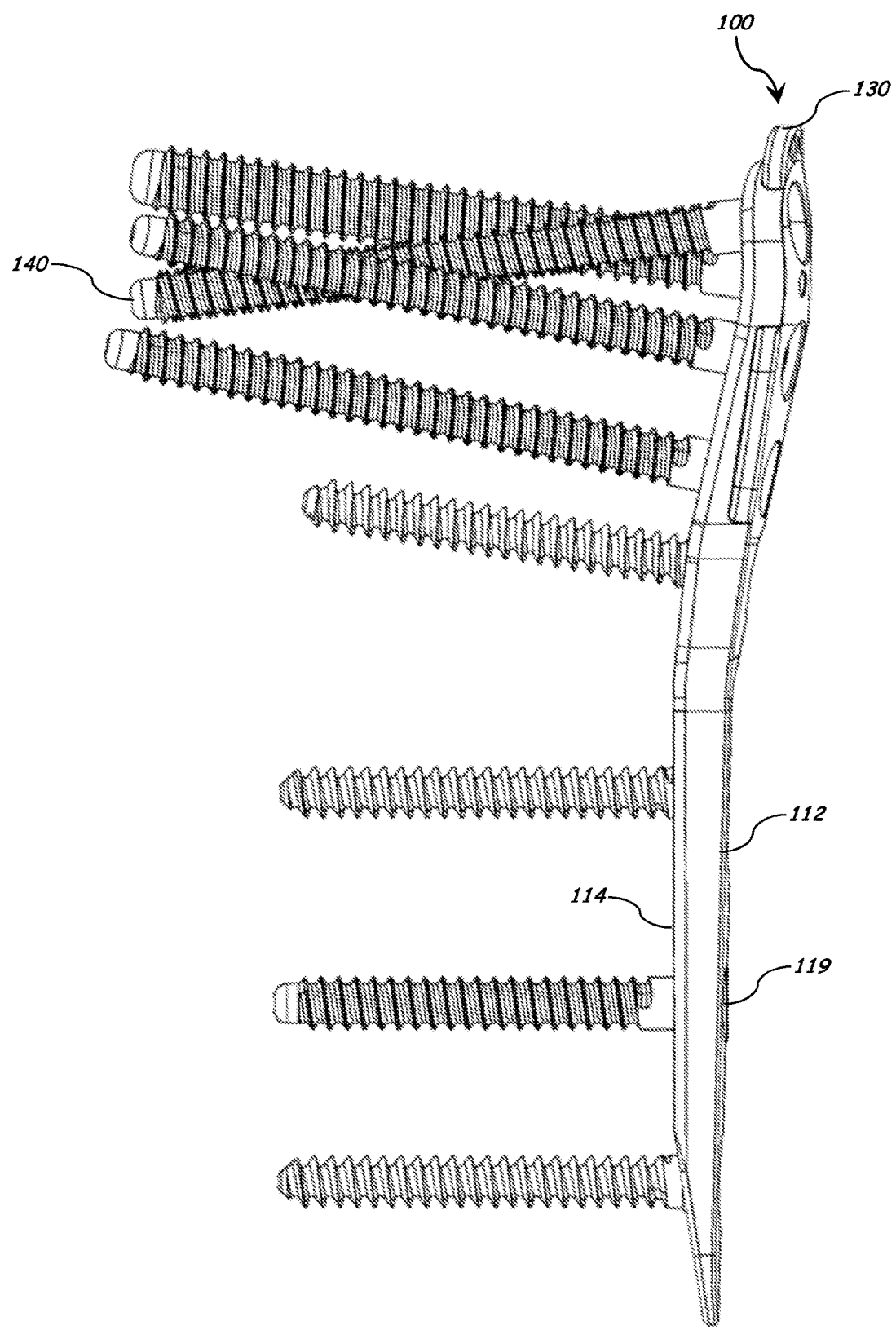
FIG. 3D shows a side perspective view of the bone plate according to FIG. 3A.
Figure 3E:
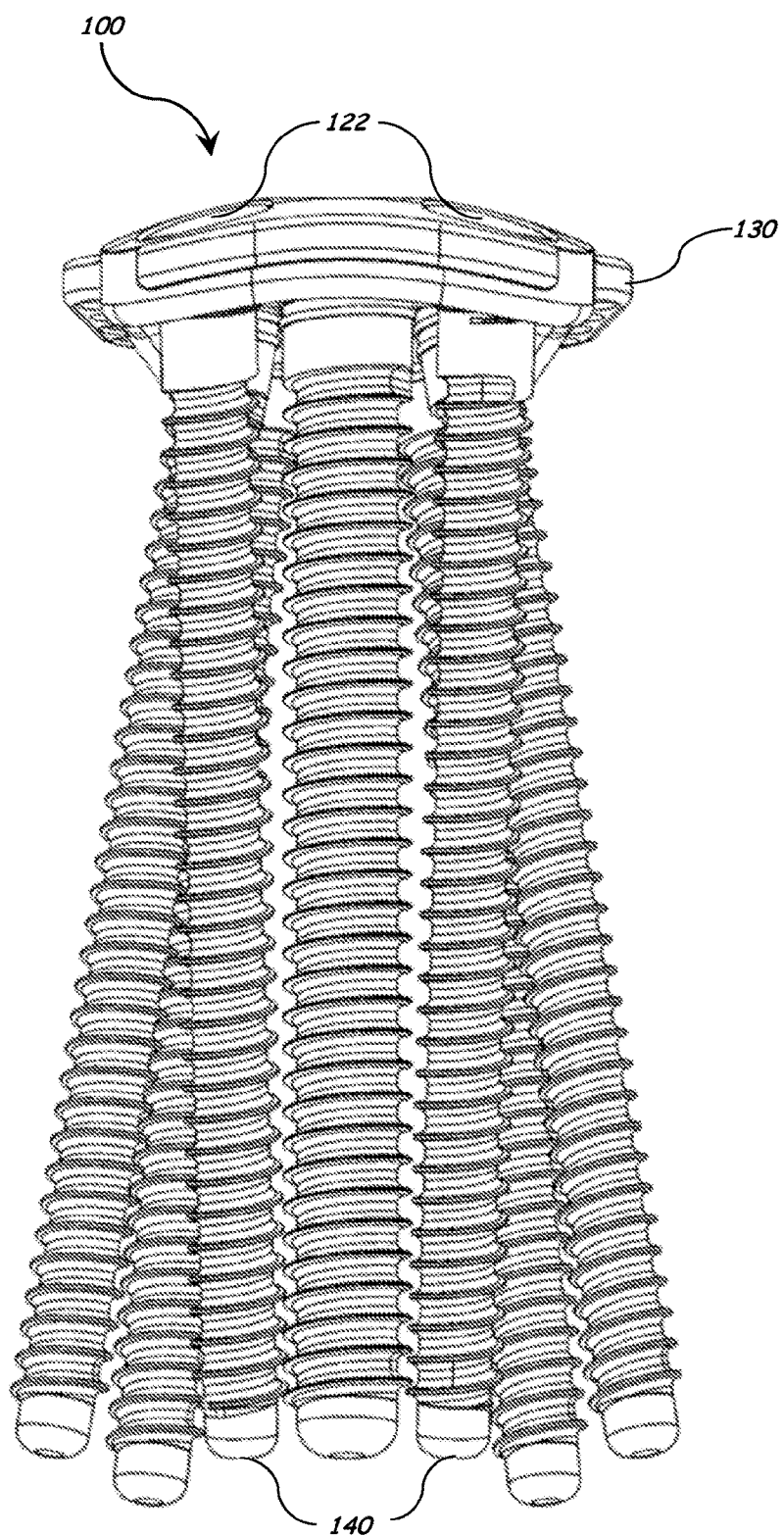
FIG. 3E shows an end perspective view of the bone plate according to FIG. 3A.

The following detailed description and the appended drawings describe and illustrate various bone plate systems, methods, and components. The description and drawings are exemplary in nature and are provided to enable one skilled in the art to make and use one or more exemplary bone plate systems and/or components, and/or practice one or more exemplary methods. They are not intended to limit the scope of the claims in any manner.

The use of "e.g.," "etc.," "for instance," "in example," and "or" and grammatically related terms indicates non-exclusive alternatives without limitation, unless otherwise noted. The use of "optionally" and grammatically related terms means that the subsequently described element, event, feature, or circumstance may or may not be present/occur, and that the description includes instances where said element, event, feature, or circumstance occurs and instances where it does not. The use of "exemplary" refers to "an example of" and is not intended to convey a meaning of an ideal or preferred embodiment. The use of "attached" and "coupled" grammatically related terms refers to the fixed, releasable, or integrated association of two or more elements and/or devices with or without one or more other elements in between. Thus, the term "attached" or "coupled" and grammatically related terms includes releasably attaching or fixedly attaching two or more elements and/or devices in the present or absence of one or more other elements in between. As used herein, the terms "proximal" and "distal" are used to describe opposing axial ends of the particular elements or features being described in relation to anatomical placement.

While the systems, methods, and components described herein are exemplified by systems and methods for internal fixation of humeral bones, the systems, methods, and components described and illustrated herein can be used to treat any short and long bones within the body of a human, including, but not limited to, animals. Skilled artisans will be able to select a suitable ailment and/or bone within the body of an animal to utilize a system and/or method described herein according to a particular embodiment based on various considerations, including the type of ailment and/or the structural arrangement at a treatment site. Example bones considered suitable to utilize a system, method, and/or component described herein include, but are not limited to, humerus, ulna, radius, clavicle, femur, tibia, fibula, tarsals, metatarsals, carpals, metacarpals and phalanges.

FIGS. 1A-F shows a bone plate configuration in accordance with the invention. Bone plate 10 may be shaped and configured for, but not limited to, fractures of the humerus. The bone plate 10 includes an upper surface 12, a lower or opposed bone-facing or bone-contacting surface 14 and a plurality of fastener holes 16, 18, 20, 22, 24 and k-wire holes 26 extending between the upper surface 12 and the opposed bone-facing surface 14 for receiving corresponding bone fasteners (not shown) and guide-wires (not shown) respectively. The bone-facing surface 14 can be shaped to substantially conform to or mate with a corresponding plate-facing surface of the bone (not shown) and may be provided with radiused or scalloped cutouts between fastener holes to limit and/or minimize contact between the bone-facing surface 14 and the bone. Limiting and/or minimizing contact between the bone plate 10 and bone has a number of biological and mechanical advantages including reduced damage to blood supply and easier plate removal. Bone plate 10 may have various sizes (various diameters and/or lengths) and may be constructed from biocompatible materials such as titanium, alloys of titanium, cobalt chrome, stainless steel, ceramics, composite materials such as carbon fiber-reinforced PEEK, resorbable materials, and combinations thereof, although one of ordinary skill in the art will know and appreciate that any biocompatible material may be used.

Referring now to FIGS. 1C-D, the upper surface 12 and the opposed bone-facing surface 14 run substantially parallel defining a first nominal thickness "$t_1$" of the bone plate 10. The bone plate 10 further includes a plurality of elevated suture hole projections or structures 30 each extending from at least a portion of a boundary or boundary edge of the bone plate 10. Each suture hole structure 30 includes an upper surface 32 and an opposed bone-facing surface 34 defining a second nominal thickness "$t_2$" of the suture hole structure 30 wherein the thickness "$t_2$" may be less than the thickness "$t_1$" of the bone plate 10, and the bone-facing surface 34 or at least a portion thereof of the suture hole structure 30 is elevated above the bone-facing surface 14 of the bone plate 10 by a distance "d" as shown in FIGS. 1C-D. The distance "d" may be in the range of about 1-4 mm. Alternatively, the distance "d" can be lesser or greater, depending on a specific surgical application.

The suture hole structures 30 can be dimensioned and configured to provide a low profile for reducing soft tissue irritation and minimizing patient discomfort. The suture hole structure 30 may have a width "w" of about 1-4 mm. The width "w" may also be lesser or greater, depending on a specific surgical application. The upper surface 32 and the lower bone-facing surface 34 of the suture hole structure 30 may be substantially parallel, at an angle relative to one another, or tapered inwardly and/or outwardly along its length or width. The upper surface 32 and the lower bone-facing surface 34 of the suture hole structure 30 each may also have a convex or concave shape, or a combination thereof.

The suture hole structures 30 each comprises a plurality of suture holes 28 extending between the upper surface 32 and the bone-facing surface 34. The suture hole structure 30 may be provided with any number of suture holes 28 as may be suitable for a specific surgical application. Alternatively, the suture hole structure 30 may have only one suture hole 28. The shape of the suture holes 28 can be circular, oval or non-circular. The suture holes 28 can be of a size adequate for passing a suture with a curved or straight suture needle and can be non-threaded for reducing suture damage.

The upper surface 32 of the suture hole structure 30 may be flush with the upper surface 12 of the bone plate 10. Alternatively, the upper surface 32 of the suture hole structure 30 can be slightly higher or lower than the upper surface 12 of the bone plate 10 and/or can have a substantially similar contour to a contour of the portion of the boundary or boundary edge of the bone plate 10 from which the suture hole structure 30 extends. The suture hole structure 30 may be at an angle with respective to the bone plate 10. The suture hole structure 30 may have at least a portion of its body being as thick or thicker than the bone plate 10 as long as at least a portion of the bone-facing surface 34 of the suture hole structure 30 is elevated above the bone-facing surface 14 of the bone plate 10 to provide a suture-clearance or spacing "d" for easy access to the suture holes 28.

The suture hole structure 30 can be permanently or removably attached or coupled to the bone plate 10 by any attachment means known to one skilled in the art. The suture hole structures 30 and the bone plate 10 can be an unitary device machined from a single block of materials, or can also be a multi-component device which can be assembled before or during surgery to provide the surgeon the flexibility in designing the bone plate to meet his or her needs.

An alternative embodiment of the present invention (not shown) includes a bone plate substantially similar to the bone plate 10 in FIGS. 1A-F, wherein the suture hole structure or structures may be folded toward the bone to provide a low profile implant. One method of manufacturing such an implant is to have the portion of the suture hole structure proximate the boundary or boundary edge of the bone plate be thinner than the remaining part of the suture hole structure to allow the surgeon to bend or fold the suture hole structure toward the bone after passing a suture for reducing soft tissue irritation and minimizing patient discomfort. Another design may require a hinged mechanism for coupling the suture hole structure to the perimeter of the bone plate.

Still another embodiment of the invention (not shown) comprises a bone plate substantially similar to the bone plate 10 in FIGS. 1A-F, wherein the bone plate is provided with a rail extending along its periphery or boundary edge. One or more suture hole structures similar to the suture hole structure 30 are coupled to the rail. This configuration provides the surgeon the flexibility to reposition the suture hole structure(s) anywhere on or along the bone plate to meet his or her specific surgical applications and needs.

According to another embodiment, the bone plate 10 can be provided with a single continuous suture hole structure (not shown) surrounding the boundary or boundary edge of the bone plate 10. This feature provides the surgeon the flexibility of attaching any muscles associated with the fractured bone to any locations on the plate to meet his or her needs for a specific surgical application.

These and other similar variations and modifications may be made without departing from the scope of the present invention.

Figure 4A:
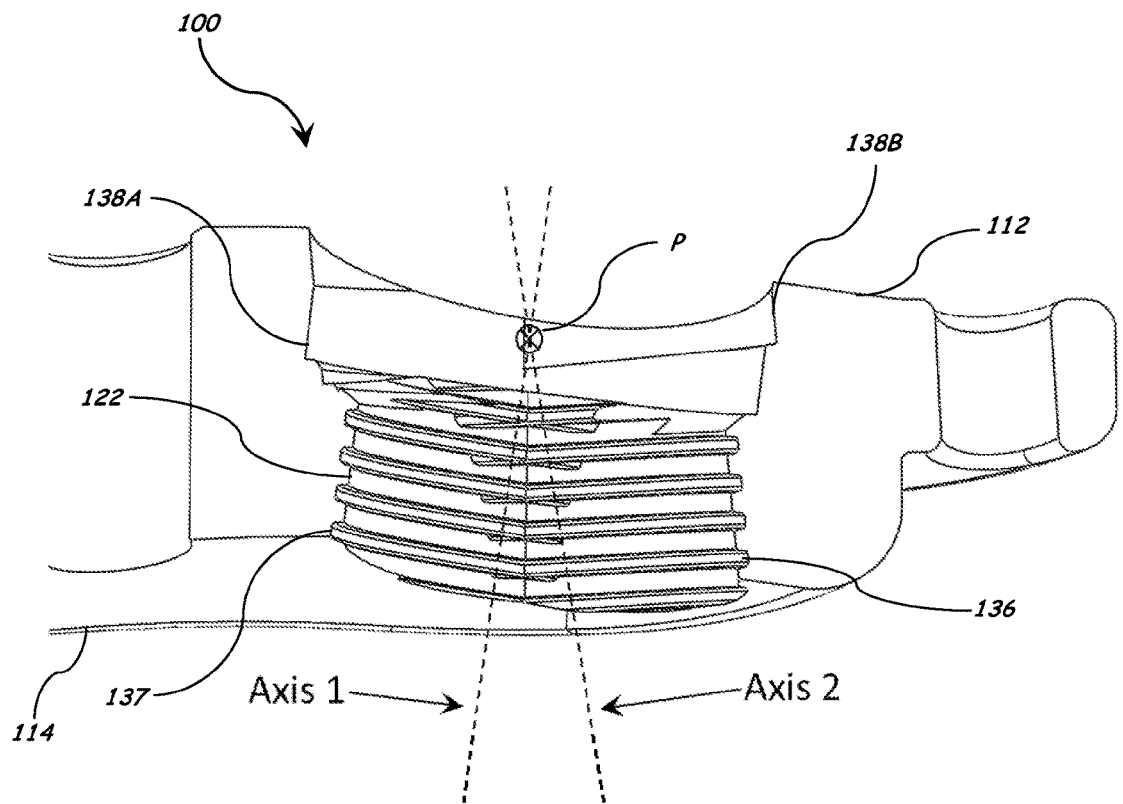
FIG. 4A shows a cross sectional view of the bone plate shown in FIG. 3A taken along sectional line 4A-4A of FIG. 3A.
Figure 4B:
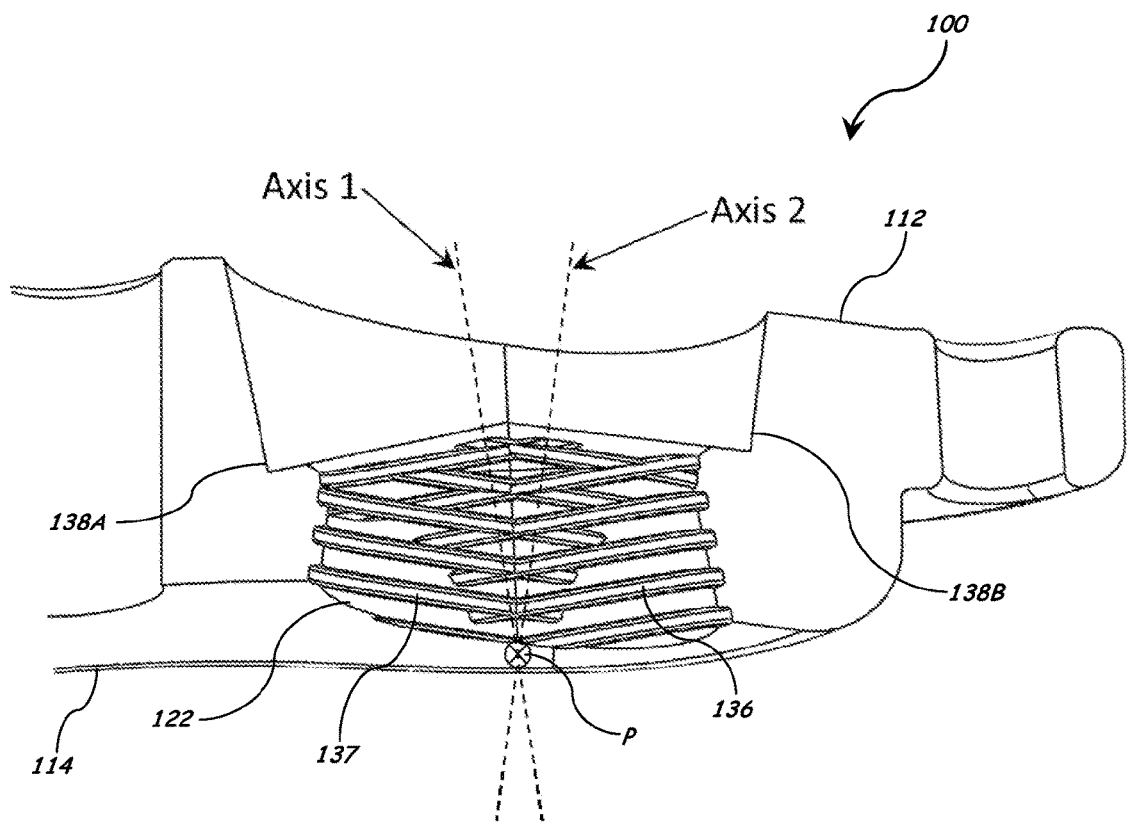
FIG. 4B shows an alternative embodiment of the threaded hole shown in FIG. 4A.

Referring to FIGS. 2A-E, 3A-E, bone plate 100 is configured substantially similar to bone plate 10 with screws 140, 160 inserted. Bone plate 100 comprises elevated suture hole structures 130 each includes a plurality of suture holes 128. The bone plate 100 is further provided with, but not limited to, two fastener holes 122 each formed with two sets of threads having intersecting axes, also referred to as bi-axial fastener holes in some embodiments. In some embodiments (not shown), the fastener holes 122 each may have more than two sets of threads with intersecting axes, depending on a specific surgical application. Where the axes cross is the intersect point or pivot point "P" which can be determined during manufacturing to be either within the fastener hole 122, or within the fastener hole 122 and generally in the same plane as the upper surface 112 of the bone plate 100 as shown in FIG. 4A, or within the fastener hole 122 and generally in the same plane as the bone-facing surface 114 of the bone plate 100 as illustrated in FIG. 4B. The provision of these bi-axial fastener holes 122 in the bone plate 100, particularly in the proximal or head portion of the bone plate 100, offers the surgeon with choice of two different and opposed trajectories, such as superiorly and inferiorly as illustrated in FIGS. 2A-E and FIGS. 3A-E respectively, for locking the bone fasteners 140 relative to the bone plate 100.

The two intersecting axes, axis 1 and axis 2, as illustrated in FIGS. 4A-B, may be configured to lie in a plane substantially parallel to a longitudinal plane dividing the bone plate into left and right halves, and form an angle $\alpha$ of about 5-45 degrees relative to one another. However, other angles are possible. In an alternative embodiment (not shown), the fastener holes 122 may include two sets of threads with intersecting axes lying on a plane substantially parallel to a transverse or cross-section plane dividing the bone plate into proximal and distal portions.

Additionally or alternatively, the bone plate 100 can be provided with one or more fastener holes, such as fastener hole 119 located in the distal portion of the bone plate 100, formed with three sets of threads with intersecting axes, such as axis 1, axis 2, axis 3 as shown in FIG. 5, wherein the intersect point or pivot point "P" of the axes is outside the fastener hole 119 and below the bone-facing surface 114 of the bone plate 100. The fastener hole 119 may have more than three sets of threads with intersecting axes. These intersecting axes each form an angle $\theta$ of about 5-45 degrees relative to one another. However, other angles are possible.

The bi-axial and tri-axial fastener holes 122, 119 can be formed in one of two methods. Referring to FIGS. 4A-B, the bi-axial hole 122 may be formed by drilling a hole along axis 1 at a predetermined angle relative to the bone plate 100 and another hole along axis 2 at a different predetermined angle relative to the bone plate 100 so that axis 1 and axis 2 intersect at a point "P" proximate the upper surface 112 of the bone plate 100, or proximate the bone-facing surface 114 of the bone plate 100. The countersinks 138A, 138B may be formed during or after drilling the holes. The threads 136, 137 may be right-hand threads and cut out with a machine tap that follows the individual axes of the respective drilled holes. The bi-axial hole, such as fastener hole 122, may have, but is not limited to, an oval or elongated shape from a top view of the fastener hole 122. The shape and size of the bi-axial holes 122 may vary throughout the thickness of the bone plate 100. Alternatively, the threads 136, 137 of the bi-axial hole 122 may not extend all the way from the upper surface 112 to the bone-facing surface 114 of the bone plate 100. A smooth, non-threaded, conical inward or outward taper may be formed into the upper or lower region of the bi-axial hole 122 (not shown) to provide for a broader range of angles for angularly positioning a non-locking bone fastener.

The tri-axial hole 119 as illustrated in FIG. 5 can be formed by drilling three separate holes through the bone plate 100 such that the hole axes intersect at a point below the bone facing surface 114 of the bone plate 100. The method of forming the countersinks and the threads may be similar to that of forming the bi-axial fastener hole 122.

Different types of screws/pegs may be used with the bi-axial and tri-axial holes 122, 119, including non-locking, locking, unidirectional and omnidirectional or surgeon-directed screws. One type of screw may be a locking screw that has a conically-tapered or cylindrical threaded head such as bone screws 140. The external threads of heads of the screws 140 may mate with the internal threads 136, 137 of the holes 122, 119 to angularly lock the screws/pegs 140 while the helical threads of the shaft of the screws/pegs 140 engage the bone.

The bone plate 100 further includes a non-threaded elongated slot 120 configured and dimensioned to engage a substantially spherical or hemi-spherical screw-head of a bone screw, such as bone screw 160. Alternatively, a conically shaped screw head, with or without threads, may engage the elongated slot 120. The elongated slot 120 may have a concave, substantially spherical portion or recess that opens toward the upper surface 112 of the bone plate 100. When the shaft of a bone screw 160 having a spherical or semi-spherical head is located eccentrically in the elongated slot 120, the spherical or semi-spherical head may engage the recess and bias the bone plate to provide compression of the bone fracture. The bone plate 100 may be provided with other non-locking, locking and/or combination holes for specific surgical applications.

The bone plate system of the present invention provides for any tissue repair and attachment of soft tissue to bone as part of fracture management repair. Although there have been described and illustrated herein various embodiments of a humeral fracture bone plate, it is not intended that the invention be limited thereto, as it is intended that the invention be as broad in scope as the art will allow and that the specification be read likewise. Thus, while the exemplary embodiment is described and illustrated as a humeral fracture bone plate system, it is appreciated that the system is well adapted to bone fractures of any bones with or without an articular convex-shape surface. Thus, the system of the invention could similarly be used to treat fracture of other bones, e.g., a fracture of the femoral head, a fracture of a radius. In addition to the use of the present bone plate system for treatment of fractures, it is appreciated that the present invention may also be used in the treatment of osteotomies and non-unions of the proximal humerus and other bones with or without an articular convex-shape surface.

The principles, preferred embodiments and modes of operation of the present invention have been made apparent in the foregoing description.

Although the embodiments are numbered with, for example, "first," "second," or "third," or "fourth," the ordinal numbers do not imply priorities of the embodiments.

Since many modifications, variations and changes in detail can be made to the described embodiments of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. A bone plate system for securing to a bone, the system comprising:

An elongated bone plate extending along a longitudinal axis, the bone plate having:
a first boundary edge wrapping an entirety of the bone plate,
a first upper surface connected to a first upper side of the first boundary edge,
a first opposed bone-facing surface connected to an opposite first lower side of the first boundary edge, and
at least one fastener hole extending through the first upper surface and the first bone-facing surface, the at least one fastener hole is elongated along an axis traversing the longitudinal axis of the plate, and includes a plurality of sets of threads with intersecting axes, wherein the intersecting axes of the plurality of sets of threads lie in a plane substantially parallel to at least one of a longitudinal plane which divides the plane into left and right portions and a transverse plane which divides the bone plate into proximal and distal portions, the at least one fastener hole configured to receive a bone fastener configured to couple the bone plate to the bone,
a distance measured between the upper side and the lower side of the first boundary edge defining a bone plate thickness of the bone plate,
a distance measured between a proximal portion of the boundary edge to a distal portion of the boundary edge along the longitudinal axis of the bone plate defining a bone plate length of the bone plate,
a distance measured between a lateral portion of the boundary edge to an opposed lateral portion of the boundary edge traversing the longitudinal axis of the bone plate defining a bone plate width of the bone plate; and
a plurality of suture hole structures monolithically formed with the bone plate and projecting from the first boundary edge of the bone plate, spaced away from each another along the boundary edge, each of the plurality of suture hole structures including:
a second boundary edge partially wrapping the suture hole structure,
a second upper surface connected to a second upper side of the second boundary edge, and flush with the first upper surface of the bone plate,
a second opposed bone-facing surface connected to an opposite second lower side of the second boundary edge, and elevated above the first lower surface of the bone plate,
a distance measured between the second upper surface and the second opposed bone-facing surface defining a suture hole structure thickness of the suture hole structure, and
a plurality of suture through holes extending through the second upper surface and the second opposed bone-facing surface of the suture hole structure;
the plurality of suture hole structures comprising:
a first suture hole structure projecting from a first lateral portion of the boundary edge in a direction traversing the longitudinal axis of the bone plate,
a second suture hole structure projecting from a second lateral portion of the boundary edge opposite to the first lateral portion in the direction traversing the longitudinal axis of the bone plate,
a third suture hole structure projecting distally from the distal portion of the boundary edge along the longitudinal axis of the bone plate,
Wherein the first suture hole structure is separated from the second suture hole structure by the width of the bone plate,
each of the suture through holes having a length defined by a distance between the second upper surface and the second bone-facing surface, the length of each suture hole is less than a length of the at least one fastener hole,
each suture hole further including a suture hole diameter that is less than a diameter of the at least one fastener hole,
each of the suture hole structures having a single side monolithically formed with the boundary edge of the bone plate and an opposed side having a length, measured in a direction alongside the longitudinal axis, less than the first side and projecting away from the bone plate; and
wherein the thickness of any of the suture hole structures is less than the thickness of the bone plate.

2. The bone plate system of claim 1, wherein the distance between the first bone-facing surface of the bone plate and any of the second bone-facing surfaces of the plurality of suture hole structures is less than 4 mm.

3. The bone plate system of claim 1, wherein the second upper surface of the suture hole structure has a similar contour to a contour of a portion of the boundary edge of the bone plate free from contact with any of the plurality of suture hole structures.

4. The bone plate system of claim 1, wherein the second bone-facing surface of the suture hole structure is substantially parallel to the first bone facing surface of the bone plate.

5. The bone plate system of claim 1, wherein the fastener hole comprises a countersunk region, a middle threaded region, and a lower smooth, non-threaded region.

6. The bone plate system of claim 1, wherein the fastener comprises a head having a thread for forming a threaded connection with at least one of the sets of threads of the fastener hole.

7. The bone plate system of claim 1, wherein at least one of the plurality of sets of threads is selected from a group consisting of left-hand threads and right-hand threads.

8. The bone plate system of claim 1, wherein the bone plate further comprises a second fastener hole having three sets of threads with intersecting axes.

9. The bone plate system of claim 8, wherein the bone plate further comprises an elongated slot having at least a portion of an inner wall surface being smooth for receiving a non-locking fastener.

10. The bone plate system of claim 8, wherein the bone plate includes an opening defined by two adjacent threaded holes communicating with one another.

11. The bone plate system of claim 6, wherein the threads of the fastener hole engage the bone fastener at a variable angle relative to the bone plate.

12. The bone plate system of claim 1, wherein the intersecting axes form an angle of about 5 to 45 degrees relative to the bone plate.

* * * * *